United States Patent [19]

Screttas

[11] 3,932,545

[45] Jan. 13, 1976

[54] ALKALI METAL-CONTAINING, ORGANOMETALLIC PRODUCTS

[75] Inventor: Constantinos G. Screttas, Athens, Greece

[73] Assignee: The National Hellenic Research Foundation, Athens, Greece

[22] Filed: Apr. 8, 1974

[21] Appl. No.: 458,582

[52] U.S. Cl. ..... 260/665 R; 252/431 M; 260/297 R; 260/329 ME; 260/332.3 R; 260/632 A
[51] Int. Cl.² .......................... C07F 1/00; C07F 3/00
[58] Field of Search ........ 260/665 R, 632 A, 297 R, 260/329 ME, 332.3 R; 252/431 L

[56] References Cited
UNITED STATES PATENTS

| | | | |
|---|---|---|---|
| 2,543,406 | 2/1951 | Hill | 260/632 A X |
| 2,856,391 | 10/1958 | Diem | 260/665 R X |
| 3,285,894 | 11/1966 | Lim et al | 260/632 A |

OTHER PUBLICATIONS

Brown et al, J. Organometallic Chemistry, V. 3, pp 1–6, (1965).
Rochow et al., The Chem. of Organometal. Cpds., John Wiley and Sons, Inc., N.Y., pp. 54,55,57, (1957), pp. 68–76.
Chemical Abstracts, Vol. 63, 7027b, (1965).
Chemical Abstracts, Vol. 74, 127174t, (1971).
Chemical Abstracts, Vol. 78, 111825c, (1973).
Schlosser, J. Organometal. Chem., V. 8, pp 9–16, (1967).

*Primary Examiner*—Helen M. S. Sneed
*Attorney, Agent, or Firm*—Morton, Bernard, Brown, Roberts & Sutherland

[57] ABSTRACT

An alkali metal-containing, organometallic product, which is hydrocarbon-soluble, is prepared by reacting an organo-alkali metal reactant in which the alkali metal atom is bonded to a carbon atom, e.g. cyclohexyl-lithium, with a di(organooxy)-alkaline earth metal reactant, e.g. di-n-butoxy-magnesium, in an organic solvent at about −20° to +120°C. The organo-alkali metal reactant can be prepared by reacting an organo halide with an alkali metal, and this can be done in situ, i.e. in the presence of the di(organooxy)-alkaline earth metal reactant. The organometallic product has approximately the same chemical reactivity as the organo-alkali metal reactant from which it is prepared, but is more soluble in hydrocarbon solvents.

10 Claims, No Drawings

ALKALI METAL-CONTAINING, ORGANOMETALLIC PRODUCTS

This invention relates to alkali metal-containing, organometallic compounds. More specifically, it relates to organometallic products that exhibit approximately the same chemical reactivity as organo-alkali metal compounds in which the alkali metal atom is bonded directly to a carbon atom, but are more hydrocarbon-soluble.

Organo-alkali metal compounds containing alkali metal-to-carbon bonds, such as phenyl-lithium, cyclohexyl-lithium, n-butyl-lithium, 1,4-dilithiobutane, phenyl-sodium, 2-pyridylmethyl-sodium, and n-butyl-sodium, are known compounds having several and varied uses. For example, they can be reacted with a ketone to produce a tertiary alcohol salt (e.g., cyclohexyl-sodium can be reacted with benzophenone to produce α-cyclohexyl-α-phenylbenzyloxy sodium); they can be reacted with carbon dioxide to make a carboxylic acid salt (e.g., cyclohexyl-lithium can be reacted with carbon dioxide to obtain lithium hexahydrobenzoate; they can be used to catalyze addition polymerization reactions (e.g., n-butyl-sodium can catalyze the homopolymerization of isoprene to obtain isoprene rubber); and they can be used as metalating agents to prepare weaker organometallic bases (e.g., isobutyl-sodium can be reacted with benzene to obtain phenyl-sodium).

A common drawback, however, of using such organoalkali metal compounds as reactants and catalysts is their low solubility in hydrocarbon solvents, requiring that they be used in solution in more polar solvents, such as ethers, which are more expensive, more flammable, and more of a health hazard than hydrocarbon solvents. Furthermore, polar solvents sometimes interfere with the desired reaction.

When present in conjugated diene polymerization systems, for example, polar solvents exert a disruptive effect on the mode of addition of the diene units, resulting in diene polymers having undesirably high amounts of 1,2- or 3,4-content. Polar solvents cause a relatively low cis content in polyisoprene, for example, and a relatively high vinyl content in polybutadiene. This is especially disadvantageous when it is desired to use such polymers as low temperature elastomers, for the lower the 1,2- or 3,4-content in the polymer, the lower will be its freeze point.

By this invention is provided means for converting an organo-alkali metal compound having an alkali metal-to-carbon bond into an alkali metal-containing, organometallic compound having approximately the same usefulness as a chemical reactant or catalyst as the organo-alkali metal compound, but being more soluble in hydrocarbons than the organo-alkali metal compound. This is accomplished by reacting the organo-alkali metal compound with a di(organooxy)-alkaline earth metal compound in an organic solvent at about −20° to +120°C. The product of the reaction is an alkali metal-containing, organometallic compound which possesses the same organo functionality as the organo-alkali metal compound from which it is prepared. That organo functionality can be replaced, if desired, by a less basic organo group by subjecting the organometallic compound to a transmetallation reaction with an appropriate organic compound.

The di(organooxy)-alkaline earth metal reactants used in the present invention are barium, calcium, strontium, or magnesium compounds. The elements of the organooxy groups are preferably selected from the group consisting of carbon, hydrogen, oxygen, nitrogen, sulfur, and phosphorus. The organo moieties of the organooxy groups preferably consist of one or more radicals selected from the group consisting of hydrocarbyl, ether, thioether, dihydrocarbyl amino, and dihydrocarbyl phosphino radicals. Examples of suitable organooxy groups are alkoxy groups, alkoxyalkoxy groups, N,N-dialkylaminoalkoxy groups, alkylthioalkoxy groups, and P,P-diarylphosphinoalkoxy groups. Each organooxy group preferably has 1 to 18 carbon atoms, most preferably 3 to 9 carbon atoms. As examples of suitable di(organooxy)-alkaline earth metal reactants may be mentioned bis[2-(N,N-dimethylamino)ethoxy]-magnesium; di(methylthiobutoxy)-calcium; bis[3-(P,P-diphenyl phosphino)propoxy]-barium; di-n-butoxymagnesium; di(2-methoxyethoxy)-magnesium; di(2-methoxyethoxy)-calcium; di-(2-ethoxyethoxy)barium; and di(2-methoxyethoxy)-strontium.

Preparation of the di(organooxy)-alkaline earth metal compound can be by methods known in the art, for example as described in "Metal Alkoxides" by D. C. Bradley (Volume 2 of "Progress in Inorganic Chemistry" by Interscience Publishers, New York, 1960).

The organo-alkali metal reactants used in the present invention are sodium or lithium compounds wherein each alkali metal atom is bonded to a carbon atom of the organo moiety. The organo moieties preferably have 1 to 20, most often 1 to 12, carbon atoms, can be aliphatic, cycloaliphatic, or aromatic, and can be saturated or ethylenically or acetylenically unsaturated. The elements of the organo moiety are preferably selected from the group consisting of carbon, hydrogen, oxygen, nitrogen, sulfur, and phosphorus. Preferred organo moieties are those consisting of one or more radicals selected from the group consisting of hydrocarbyl, ether, thioether, and pyridinyl radicals. Examples of suitable organo groups are cycloalkyl, alkyl, aryl, aralkyl, alkenyl, pyridylalkyl, aralkynyl (such as phenylacetylenyl), cyclothioalkenyl (such as thiophenyl), and aryloxyalkyl radicals. The organo-alkali metal reactant may be monofunctional or polyfunctional (e.g., difunctional) as regards the alkali metal sites on the compound. Some of the most commercially important organo-alkali metal reactants for use in the present invention are cyclohexyl-sodium, phenyl-sodium, benzyl-sodium, 2-pyridylmethyl-sodium, and 4-pyridylmethyl-sodium.

Preparation of the organo-alkali metal compound used in the present invention can be known methods, for example by reacting the corresponding organohalide with free alkali metal. Such a reaction, to prepare the organo-alkali metal reactant, can, if desired, be conducted in the presence of the di(organocarboxy)-alkaline earth metal reactant so as to react with the latter and yield the product of the present invention. As is known in the art, some reactions of free alkali metal with a relatively slightly reactive organo halide may require that the alkali metal first be activated by treating it with a small amount of a more reactive organo halide. Thus, for instance, when preparing cyclohexyl-lithium by reacting chlorocyclohexane with lithium metal, the reaction will be greatly facilitated if the lithium metal is first treated with a small amount of a more reactive hydrocarbyl halide, such as n-butyl chloride.

The reaction between the organo-alkali metal compound and the di-(organooxy)-alkaline earth metal compound is conducted in an organic solvent at a temperature of about −20 to +120°C., preferably about 0° to 60°C. Any organic solvent which will not interfere with the reactants or the desired product under the conditions of the reaction can be employed. Hydrocarbon solvents are preferred, such as the alkanes and cycloalkanes of 5 to 10 carbon atoms, benzene, and alkylated benzenes, e.g. the methyl-substituted benzenes. Some solvents might even be used in reaction systems in which they would react with the desired product if the mixture were held at reaction temperature for an extended period of time. In such a system, the obvious precaution to take to avoid loss of the desired product is to terminate the reaction and recover the desired product as soon as the reaction is substantially complete. An example of such a system is the reaction of phenyl-sodium with di-n-butoxy-magnesium in toluene, at room temperature. The desired organometallic product, having much the same reactivity as the phenyl-sodium reactant, will be formed but, if not removed from the reaction mixture, will undergo a transmetalation reaction with the toluene, replacing the phenyl functionality in the product with a tolyl functionality.

The products of the present invention exhibit generally the same reactivity as the organo-alkali metal compounds from which they are prepared, and they contain both the alkali metal functionality and the organo functionality of the organo-alkali metal reactant. Thus, for example, the product obtained by reacting phenyl-lithium with a di(organooxy)-alkaline earth metal compound can, in turn, be reacted with carbon dioxide to yield lithium benzoate, or can be reacted with benzophenone to yield triphenylcarboxy lithium. Also, as alluded to above in the discussion of choice of solvent, the organo functionality of a product of the present invention can be exchanged for a less basic organo group by reaction with the corresponding organic compound, yielding a different product, still of the present invention. The phenyl functionality in the reaction product of phenyl-lithium with a di(organooxy)-alkaline earth metal, for example, can be replaced by the less basic tolyl group by reacting the product with toluene. Such a product will take on the reactivity characteristics of tolyl-lithium, rather than phenyl-lithium, as the exchange of tolyl functionality for phenyl functionality progresses.

Similar transmetalation reactions, wherein the metalating agent is one of the prior art organo-alkali metal compounds having an alkali metal-to-carbon bond, are described in Neuer's "Methods of Preparative Organic Chemistry", Volume V, pp. 284-286 (Editor: W. Foerst). As there described, a n-amyl functionality in an organo-alkali metal compound can be replaced by the less basic vinyl functionality by reacting the compound with ethylene; also a phenylisopropyl functionality can be replaced by the less basic 2-methylallyl functionality by reacting with isobutene; a n-butyl functionality can be replaced by the less basic phenyl functionality by reacting with benzene; a triphenylmethyl functionality can be replaced by the less basic 9-fluorenyl functionality by reacting with fluorene, etc. The organometallic products of the present invention can undergo these same transmetalation reactions, generally at temperatures of −20° to +120°C., preferably at 0° to 60°C. The organic compounds with which they will react in that manner are compounds which, by removal of a hydrogen atom, provide a less basic organo group than the organo functionality which the organometallic product obtained from the organo-alkali metal reactant. Generally suitable for that purpose are organic compounds having 2 to 20, preferably 2 to 12, carbon atoms. They can be aliphatic, cycloaliphatic, or aromatic, and can be saturated or ethylenically or acetylenically unsaturated. The elements of such organic compounds are preferably selected from the group consisting of carbon, hydrogen, oxygen, nitrogen, sulfur, and phosphorus. Preferred compounds are those consisting of one or more radicals selected from the group consisting of hydrocarbyl, ether, thioether, and pyridinyl radicals. Examples of suitable types of organic compounds are hydrocarbons, cyclothioalkenes (such as thiophene), pyridylalkanes (such as picoline), and aryloxyalkanes.

The invention will be better understood by reference to the following examples, which are offered for illustration purposes only, and not for limitation. In each of the examples, the reaction was conducted in a round bottom flask equipped with dropping funnel, stirrer, and reflux condenser.

EXAMPLE I

Preparation of Reaction Product of Cyclohexyl-lithium (Prepared in situ) and Di-n-butoxy-magnesium Into the reaction vessel was placed 0.5 gram atom of lithium metal dispersion. The vessel was evacuated and then filled with high purity argon gas to atmospheric pressure. One hundred ml. of dry pentane was added, followed by 0.5 ml. of n-butyl chloride to activate the lithium. Thirty g. of di-n-butoxy-magnesium powder was then introduced rapidly, followed by the dropwise addition of a solution of 0.2 mole of chlorocyclohexane in 100 ml. of dry pentane, with vigorous stirring. The rate of addition was adjusted so as to maintain a steady, gentle reflux of the solvent throughout the addition. Stirring was continued for 1 hour after completion of the addition. The reaction mixture was filtered through a glass filter under argon to give a clear filtrate in which lithium-containing organometallic product was dissolved.

The filtrate was tested for cyclohexyl-lithium type of activity by reacting it with solid carbon dioxide (slurried in diethyl ether) followed by treatment with dilute sulfuric acid. The resultant product was hexahydrobenzoic acid, in 79% yield, based on the amount of chlorocyclohexane used, confirming that the organometallic product had the same reactivity toward carbon dioxide as does cyclohexyl-lithium, which, however, is insoluble in n-pentane.

EXAMPLE II

Preparation of Reaction Product of n-Butyl-lithium and Di-n-butoxy-magnesium

Into the reaction vessel was placed 0.02 mole of di-n-butoxy-magnesium, following which one neck of the vessel was closed with a rubber septum and the other neck was joined to a vacuum line. The flask was evacuated, then filled with argon to atmospheric pressure. 10 ml. of a 1.7 molar solution of n-butyl-lithium in n-pentane was introduced with a syringe through the rubber septum. The di-n-butoxy-magnesium at first was undissolved but, upon stirring, a clear solution was formed. The solution was freeze-dried, leaving a lithium-containing, organometallic product in the form of a viscous liquid.

The product was dissolved in 5 ml. of dry benzene and analyzed by Nuclear Magnetic Resonance (NMR) spectroscopy. The spectrum exhibited a diffused triplet at about 10.55τ, which is distinct from that exhibited by n-butyl-lithium, which is about 10.83τ. The solution was tested for n-butyl-lithium type of activity by reacting it with carbon dioxide, followed by treatment with dilute sulfuric acid. The resultant product was valeric acid, in 95% yield, based on the amount of n-butyl-lithium used, confirming that the organometallic product had the same reactivity toward carbon dioxide as does n-butyl-lithium.

EXAMPLE III

Preparation of Reaction Product of n-Butyl-sodium (Prepared in situ) and Di(2-methoxy-ethoxy)-magnesium Into the reaction vessel were placed 0.4 gram atom of sodium metal, cut in small pieces, 200 ml. of dry n-pentane, and 35 grams of powdered di(2-methoxyethoxy)-magnesium. Into that mixture was added n-butyl chloride, dropwise with continuous stirring, until the sodium metal was completely reacted, which required 26 ml. of the n-butyl chloride. The resultant reaction mixture was filtered through a glass filter. The clear, colorless filtrate, in which sodium-containing, organometallic product was dissolved, was reacted with solid carbon dioxide (crushed and slurried in diethyl ether) followed by treatment with dilute sulfuric acid to give 17.3 grams of valeric acid (an 85% yield, based on the amount of n-butyl chloride used), confirming that the organometallic product had the same reactivity toward carbon dioxide as does n-butyl-sodium, which, however, is insoluble in n-pentane.

EXAMPLE IV

Preparation of Reaction Product of Phenyl-sodium and Di(2-methoxyethoxy)-calcium A suspension of phenyl-sodium in toluene was prepared by reacting 0.45 gram atom of sodium with 0.2 mole of chlorobenzene in 200 ml. of toluene.

To the suspension was added 0.2 mole of di(2-methoxyethoxy)-calcium. On stirring the mixture, the phenyl-sodium reacted and went into solution. On carbonation, followed by treatment with dilute sulfuric acid, the mixture gave 14.6 grams of benzoic acid (a 60% yield, based on the amount of chlorobenzene used), illustrating that the sodium-containing, organometallic product had the same reactivity toward carbon dioxide as does phenyl-sodium.

EXAMPLE V

Preparation of Reaction Product of n-Butyl-lithium and Di(2-methoxyethoxy)-calcium To 0.02 mole of di(2-methoxyethoxy)-calcium was added 10 ml. of a 1.7 molar solution of n-butyl-lithium in n-pentane at about −10°C. The mixture was stirred and reacted for 2 hours at −10° to 0°C., yielding a dissolved, lithium-containing, organometallic product.

To the resultant mixture was then added 10 ml. of dry toluene. The mixture was stirred and reacted overnight, during which period the liquid turned a light yellowish-green in color and a precipitate formed.

The resultant mixture was reacted with carbon dioxide, followed by treatment with dilute sulfuric acid, giving an 80% yield of phenylacetic acid, based on the amount of n-butyl-lithium used, thus revealing that the product of the first reaction entered into a transmetalation reaction with the toluene to replace the butyl functionality in the first product with the less basic tolyl functionality. The second product, also a hydrocarbon-soluble, lithium-containing, organometallic compound, demonstrated the same reactivity towards carbon dioxide as is exhibited by tolyl-lithium, which, however, is insoluble in hydrocarbons. k

EXAMPLE VI

Preparation of Reaction Product of n-Butyl-lithium and Di(2-ethoxyethoxy)-barium Three grams of powdered barium hydride was stirred and reacted overnight with 2 ml. of 2-ethoxyethanol in 10 ml. of toluene, under argon atmosphere, yielding a slurry of di(2-ethoxyethoxy)-barium in toluene. To the slurry was added 10 ml. of a 1.7 molar solution of n-butyl-lithium in n-pentane. The mixture was stirred for 3 hours at room temperature, during which time a reaction ensued between the di(2-ethoxyethoxy)-barium, the n-butyl-lithium, and the toluene to give a partly hydrocarbon-soluble, lithium-containing, organometallic product having tolyl functionality.

The reaction mixture was carbonated and then treated with dilute sulfuric acid to provide an 80% yield (based on the amount of n-butyl-lithium used) of phenylacetic acid, illustrating that the lithium-containing organometallic product had the same reactivity toward carbon dioxide as does tolyl-lithium, which, however, is insoluble in hydrocarbons.

EXAMPLE VII

Preparation of Reaction Product of Phenyl-lithium and Di(2-methoxyethoxy)-strontium To a suspension of 0.01 mole of phenyl-lithium in 10 ml. of dry benzene was added 2.5 grams of di(2-methoxy-ethoxy)-strontium. On stirring the mixture, all of the suspended phenyl-lithium reacted and went into solution.

Carbonation of the reaction mixture, followed by treatment with dilute sulfuric acid, produced benzoic acid in 89% yield, based on the amount of phenyl-lithium used, illustrating that the lithium-containing organometallic product had the same reactivity toward carbon dioxide as does phenyl-lithium.

EXAMPLE VIII

Preparation of Reaction Product of Cyclohexyl-sodium and Di-(2-ethoxyethoxy)-magnesium One hundred milliliters of dry n-pentane, 6.0 g. of sodium metal in pieces, 18 ml. of chlorocyclohexane, and 14 g. of di-(2-ethoxyethoxy)-magnesium were stirred under argon. The stirring rate was gradually increased until the characteristic blue coloration appeared. Stirring was continued at such a rate that a gentle reflux of the solvent was maintained without external heating. The reaction was complete in about 3.5 hours. On standing, a clear supernatant separated from the reaction mixture. Titration of a 1.0 ml. aliquot of the supernatant with standard acid revealed the aliquot to be 2.1 M in total alkalinity. The mixture was filtered through a glass filter under argon, and the filtrate was poured over a slurry of Dry Ice in diethyl ether. Treatment of the carbonation mixture with dilute sulfuric acid provided 8.5 g. of hexahydrobenzoic acid, representing a 95% yield, based on the amount of di-(2-ethoxyethoxy)-magnesium used.

EXAMPLE IX

Preparation of Reaction Product of Phenyl-sodium (Prepared in situ) and Di-(2-methoxyethoxy)-magnesium A mixture of 1.8 g. of diphenyl-mercury, 0.5 g. of sodium metal, 10 ml. of dry benzene, and 2.0 g. of di-(2-methoxyethoxy)-magnesium was reacted at room temperature. To the resulting mixture, containing sodium-containing, organometallic product, was added 3.0 ml. of 1-methylnaphthalene, following which the mixture was stirred for 4 hours at 50°–55°C. At the end of this period, the mixture was a brownish-red, clear solution.

Carbonation of the latter solution, followed by treatment with dilute sulfuric acid, gave 1.36 g. of naphthyl-1-acetic acid, representing a 73% yield and confirming that the reaction product of phenyl-sodium and di-(2-methoxyethoxy)-magnesium entered into a transmetalation reaction with 1-methylnapthalene in the same manner as does phenyl-sodium.

EXAMPLE X

Preparation of Reaction Product of 2-Butenyl-2-lithium and Di-(2-ethoxyethoxy)-magnesium A dispersion of 2.0 g. of lithium metal in 50 ml. of diethyl ester was placed in the reaction flask. To the dispersion was added, over a half-hour period, with stirring, 6.8 g. of a mixture of cis and trans 2-bromobutene-2 in 50 ml. of anhydrous diethyl ether. After 1 hour of additional stirring, the mixture was freeze-dried. Vacuum was applied to the residue for several hours, following which the residue was mixed with 50 ml. of dry benzene and 10 g. of di-(2-ethoxyethoxy)-magnesium. Stirring of the mixture resulted in a clear solution of lithium-containing, organometallic product.

The product solution was reacted with 9.0 g. of benzophenone dissolved in 25 ml. of benzene for 3 hours at room temperature, following which it was hydrolyzed, providing 7.6 g. (representing a 64% yield) of 1,1-diphenyl-1-hydroxy-2-methyl-butene-2, illustrating that the lithium-containing, organometallic product had the same reactivity toward benzophenone as does 2-butenyl-2-lithium.

EXAMPLE XI

Preparation of Reaction Product of 1,4-Dilithiobutane and Di-(2-ethoxyethoxy)-magnesium Twenty-one and six-tenths grams (0.1 mole) of 1,4-dibromobutane in 150 ml. of anhydrous diethyl ether was added slowly with vigorous stirring to 5.0 g. of lithium sand, suspended in 50 ml. of diethyl ether. The reaction was started by stirring for a few minutes at room temperature, after which time it was kept at −10° to −20°C. Additional stirring for 2 hours at −10° to +10°C. completed the reaction. The reaction mixture was filtered through a glass filter under argon and the filtrate was freeze-dried. Vacuum was applied to the residue for 6 hours, following which the residue was mixed with 20 g. of di-(2-ethoxyethoxy)-magnesium and 200 ml. of dry benzene. On stirring, most of the solid material went into solution, providing a hydrocarbon solution of lithium-containing organometallic product.

Filtration of the product mixture through a glass filter and carbonation of the filtrate, followed by treatment with dilute sulfuric acid, afforded 8.61 g. (59% yield) of adipic acid, thereby illustrating that the lithium-containing, organometallic product had the same reactivity toward carbon dioxide as does 1,4-dilithiobutane.

The following examples illustrate the properties of some of the compounds prepared by the present invention.

EXAMPLE XII

Ten ml. of a 1.0 Molar solution in cyclohexane of the sodium-containing, organometallic reaction product of n-butyl-sodium and di-(2-ethoxyethoxy)-magnesium was stored for 6 months, following which it was added to 3.0 ml. of 4-picoline. The resulting mixture was stored overnight at room temperature, and then mixed with 4.0 g. of benzophenone dissolved in 10 ml. of dry benzene. Stirring was continued for 4 hours without heating. Hydrolysis of the resultant mixture and removal of the excess benzophenone by steam distillation left 2.36 g (85% yield) of 1,1-diphenyl-1-hydroxy-2-(p-pyridyl)ehtane, illustrating that the sodium-containing, organometallic product had entered into a transmetalation reaction with the 4-picoline, the product of which exhibited the same reactivity toward benzophenone as does 4-picolinyl-sodium.

EXAMPLES XIII AND XIV

The same reactions as those in Example XII, but using 2-picoline and 3-picoline, instead of 4-picoline, provided 93 and 30% yields, respectively, of 1,1-diphenyl-1-hydroxy-2-(o-pyridyl)ethane and 1,1-diphenyl-1-hydroxy-2-(m-pyridyl)ethane.

EXAMPLE XV

Sodium-containing, organometallic product (0.01 Mole) of the reaction of n-butyl-sodium and di-(2-methoxyethoxy)-magnesium was provided in solution in 10 ml. of n-pentane. Two ml. of phenylacetylene was added to the solution, following which a vigorous reaction took place and a white precipitate formed. On adding 10 ml. of dry benzene to the reaction mixture, most of the solids went into solution. Carbonation of the resultant mixture followed by treatment with dilute sulfuric acid, provided 1.16 g. (an 80% yield) of phenylpropynoic acid, illustrating that the sodium-containing, organometallic product had entered into a transmetalation reaction with the phenylacetylene, the product of which exhibited the same reactivity toward carbon dioxide as does phenylacetylenyl-sodium.

EXAMPLE XVI

The same sequence of reaction as those in Example XV, but using 3.0 ml. of thiophene, rather than phenylacetylene, provided a 68% yield of 2-thienoic acid.

EXAMPLE XVII

The same sequence of reactions as those used in Example IX, but using 3.0 ml. of anisole, rather than 1-methylnaphthalene, provide 0.96 g. (a 62% yield) of 2-methoxybenzoic acid.

I claim:

1. The hydrocarbon-soluble, alkali metal-containing, organometallic product of the reaction in an organic solvent at about −20 to +120°C. of an organoalkali metal reactant with a di(organooxy)-alkaline earth metal reactant, wherein the organo moiety of the organo-alkali metal reactant has 1 to 20 carbon atoms and consists of one or more radicals selected from the group consisting of hydrocarbyl, ether, thioether, and pyridinyl radicals, each alkali metal atom of the organo-alkali metal reactant is directly bonded to a carbon atom of the organo moiety, the alkali metal is selected from the group consisting of sodium and lithium, the organooxy groups of the di(organooxy)-alkaline earth metal reactant are selected from the group consisting of alkoxy groups, alkoxyalkoxy groups, N,N-dialkylaminoalkoxy groups, alkylthioalkoxy groups, and P,P-diarylphosphinoalkoxy groups, each organooxy group has 1 to 18 carbon atoms, and the alkaline earth metal is selected from the group consisting of barium, calcium, strontium, and magnesium.

2. The product of claim 1 wherein the organo moiety of the organo-alkali metal reactant is selected from the group consisting of cycloalkyl, alkyl, aryl, aralkyl, alkenyl, pyridylalkyl, aralkynyl, cyclothioalkenyl, and aryloxyalkyl radicals, and the organo-alkali metal reactant contains up to two alkali metal atoms per molecule.

3. The product of claim 1 wherein the organo moiety of the organo-alkali metal reactant is selected from the group consisting of cyclohexyl, butyl, phenyl, benzyl, naphthyl-1-methyl, 2-butenyl-2-, 2-picolinyl, 3-picolinyl, 4-picolinyl, phenylacetylenyl, 2-thiophenyl, and phenyloxymethyl radicals.

4. A method of replacing (a) the organo functionality in the product of claim 1 that is derived from the organo-alkali metal reactant with (b) a less basic organo functionality, comprising subjecting said product to a transmetalation reaction at about −20° to +120°C. with an organic compound which, by removal of a hydrogen atom, provides a less basic organo group than (a), said organic compound having 2 to 20 carbon atoms and being selected from the group consisting of hydrocarbons, cyclothioalkenes, pyridylalkanes, and aryloxyalkanes.

5. The method of claim 4 wherein the organo moiety of the organo-alkali metal reactant is selected from the group consisting of cycloalkyl, alkyl, aryl, aralkyl, alkenyl, pyridylalkyl, aralkynyl, cyclothioalkenyl, and aryloxyalkyl radicals, and the organo-alkali metal reactant contains up to two alkali metal atoms per molecule.

6. The product of the method of claim 4.

7. The product of the method of claim 5.

8. The product of claim 1 wherein the organo-alkali metal reactant is selected from the group consisting of cyclohexyl-lithium, phenyl-lithium, n-butyl-lithium, cyclohexyl-sodium, benzyl-sodium, 2-pyridylmethyl-sodium, 4-pyridylmethyl-sodium, n-butyl-sodium, phenyl-sodium, 2-butenyl-2-lithium, and 1,4-di-lithiobutane, and the di(organooxy)-alkaline earth metal is selected from the group consisting of dibutoxy-magnesium, di(2-methoxyethoxy)-magnesium, di(2-methoxyethoxy)-calcium, di(2-ethoxyethoxy)-barium, di(2-methoxyethoxy)-strontium, bis[3-(P,P-diphenylphosphino)-propoxy]-magnesium, bis[2-N,N-dimethylamino)ethoxy]-magnesium, di(4-methylthiobutoxy)-magnesium, di(2-ethoxyethoxy)magnesium, di(methylthiobutoxy)-calcium and bis[3-(P,P-diphenylphosphino)-propoxy]-barium.

9. The method of claim 5 wherein the organo-alkali metal reactant is selected from the group consisting of cyclohexyl-lithium, phenyl-lithium, n-butyl-lithium, cyclohexyl-sodium, benzyl-sodium, 2-pyridylmethyl-sodium, 4-pyridylmethyl-sodium, n-butyl-sodium, phenyl-sodium, 2-butenyl-2-lithium, and 1,4-di-lithiobutane, and the di(organooxy)-alkaline earth metal is selected from the group consisting of dibutoxy-magnesium, di(2-methoxyethoxy)-magnesium, di(2-methoxyethoxy)-calcium, di(2-ethoxyethoxy)-barium, di(2-methoxyethoxy)-strontium, bis[3-(P,P-diphenylphosphino)-propoxy]-magnesium, bis[2-(N,N-dimethylamino) ethoxy]-magnesium, di(4-methylthiobutoxy)-magnesium, di(2-ethoxyethoxy)magnesium, di(methylthiobutoxy)-calcium and bis[3-(P,P-diphenylphosphino)-propoxy]-barium.

10. The product of the method of claim 9.

* * * * *